United States Patent
Jover et al.

(10) Patent No.: US 8,729,073 B2
(45) Date of Patent: May 20, 2014

(54) 5-METHYL-1-(NAPHTHALEN-2-YL)-1H-PYRAZOLE DERIVATIVES AND THEIR USE IN POTENTIATING THE EFFECT OF OPIOID ANALGESICS

(75) Inventors: Antoni Torrens Jover, Barcelona (ES); María Rosa Cuberes-Altisent, Barcelona (ES)

(73) Assignee: Laboratorios Del Dr. Esteve, S.A., Barcelona (ES)

(*) Notice: Subject to any disclaimer, the term of this patent is extended or adjusted under 35 U.S.C. 154(b) by 0 days.

(21) Appl. No.: 13/991,267

(22) PCT Filed: Dec. 2, 2011

(86) PCT No.: PCT/EP2011/071583
§ 371 (c)(1),
(2), (4) Date: Aug. 5, 2013

(87) PCT Pub. No.: WO2012/072781
PCT Pub. Date: Jun. 7, 2012

(65) Prior Publication Data
US 2013/0303540 A1 Nov. 14, 2013

(30) Foreign Application Priority Data
Dec. 3, 2010 (EP) .................................. 10382326

(51) Int. Cl.
*A61K 31/535* (2006.01)
*A61K 31/44* (2006.01)
*C07D 265/30* (2006.01)

(52) U.S. Cl.
CPC .................................. *A61K 31/535* (2013.01)
USPC .................... 514/231.5; 514/282; 544/106

(58) Field of Classification Search
CPC . A61K 31/535; A61K 31/485; C07D 295/023
USPC ................. 514/231.5, 282; 544/106
See application file for complete search history.

(56) References Cited

U.S. PATENT DOCUMENTS

2009/0264442 A1 * 10/2009 Cuberes-Altisent et al. ................ 514/254.05
2010/0190780 A1 * 7/2010 Laggner et al. ............. 514/227.8

FOREIGN PATENT DOCUMENTS

| WO | WO 00/20005 A1 | 4/2000 |
| WO | WO 2006/021462 A1 | 3/2006 |
| WO | WO 2007/098953 A1 | 9/2007 |

OTHER PUBLICATIONS

Merskey, IASP, Classification of chronic pain, 2nd Edition, IASP Press (2002), pp. 210-213.
International Search Report issued by the International Searching Authority (ISA/O.E.P.M.) on Jan. 9, 2012 in connection with International Application No. PCT/EP2011/071583.

* cited by examiner

*Primary Examiner* — Raymond Henley, III
(74) *Attorney, Agent, or Firm* — Gary J. Gershik; Cooper & Dunham LLP

(57) ABSTRACT

The invention relates to pyrazole derivatives of formula I having pharmacological activity

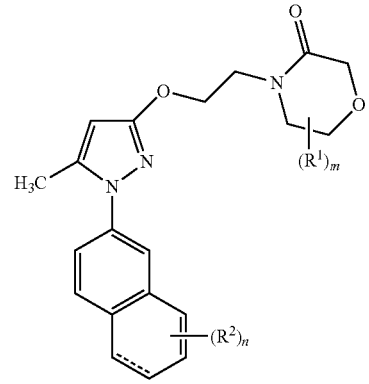

and to processes of preparation of such compounds, to pharmaceutical compositions comprising them, and to their use in therapy and/or prophylaxis of pain.

19 Claims, 3 Drawing Sheets

5-METHYL-1-(NAPHTHALEN-2-YL)-1H-PYRAZOLE DERIVATIVES AND THEIR USE IN POTENTIATING THE EFFECT OF OPIOID ANALGESICS

RELATED APPLICATIONS

This application is a §371 national stage of PCT International Application No. PCT/EP2011/071583, filed Dec. 2, 2011, claiming priority of European Patent Application No. EP10382326.6, filed Dec. 3, 2010, the contents of each of which are hereby incorporated by reference into this application.

FIELD OF THE INVENTION

The present invention relates to compounds having pharmacological activity, and more particularly to some pyrazole derivatives, to processes of preparation of such compounds, to pharmaceutical compositions comprising them, and to their use in therapy and/or prophylaxis of pain as well as their use in potentiating the analgesic effect of opioids and opiates.

BACKGROUND

The treatment of pain conditions is of great importance in medicine. There is currently a world-wide need for additional pain therapy. The pressing requirement for a specific treatment of pain conditions is documented in the large number of scientific works that have appeared recently in the field of applied analgesics.

PAIN is defined by the International Association for the Study of Pain (IASP) as "an unpleasant sensory and emotional experience associated with actual or potential tissue damage, or described in terms of such damage" (IASP, Classification of chronic pain, $2^{nd}$ Edition, IASP Press (2002), 210). Although it is a complex process influenced by both physiological and psychological factors and is always subjective, its causes or syndromes can be classified. Pain can be classified based on temporal, aetiological or physiological criteria. When pain is classified by time, it can be acute or chronic. Aetiological classifications of pain are malignant or non-malignant. A third classification is physiological, which includes nociceptive pain (results from detection by specialized transducers in tissues attached to A-delta and C-fibres), that can be divided into somatic and visceral types of pain, and neuropathic pain (results from irritation or damage to the nervous system), that can be divided into peripheral and central neuropathic pain. Pain is a normal physiological reaction of the somatosensory system to noxious stimulation which alerts the individual to actual or potential tissue damage. It serves a protective function of informing us of injury or disease, and usually remits when healing is complete or the condition is cured. However, pain may result from a pathological state characterized by one or more of the following: pain in the absence of a noxious stimulus (spontaneous pain), increased duration of response to brief stimulation (ongoing pain or hyperpathia), reduced pain threshold (allodynia), increased responsiveness to suprathreshold stimulation (hyperalgesia), spread of pain and hyperalgesia to uninjured tissue (referred pain and secondary hyperalgesia), and abnormal sensations (e.g., dysesthesia, paresthesia).

WO2006021462 and WO2007098953 describe pyrazole-containing compounds useful in the therapy of pain, in general, and, more particularly, in treatment of neuropathic pain or allodynia. These compounds have the following chemical structure:

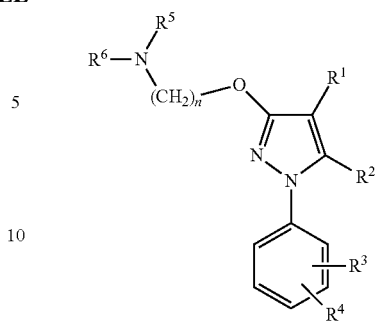

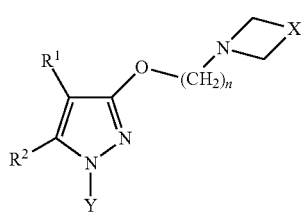

On another front, opioids and opiates are potent analgesics widely used in clinical practice. Opiates refer to alkaloids extracted from poppy pods (Opium Poppy; Papaver Somniferum) and their semi-synthetic counterparts which bind to the opioid receptors. Basically to be called an opiate one has to either be a natural opioid receptor agonist or start the refining process with one of the natural alkaloid molecules. Once chemically altered, such as the process of converting morphine into heroin, the drug is then labeled as a semi-synthetic opiate or semi-synthetic opioid—the terms can be used interchangeably. Semi-synthetic opiates (or semi-synthetic opioids) include heroin (diamorphine), oxycodone, hydrocodone, dihydrocodiene, hydromorphone, oxymorphone, buprenorphine and etorphine. In contrast, opioid is a blanket term used for any drug which binds to the opioid receptors. Opioids include all of the opiates as well as any synthesized drug that bind to opioid receptors. Synthetic opioids include methadone, pethidine, fentanyl, alfentanil, sufentanil, remifentanil, carfentanyl, tramadol, tapentadol and loperamide.

Opioid analgesics are recommended for the management of moderate to severe pain including that which occurs following surgery and trauma and in many patients with cancer.

In spite of this background, there is still a need in the art to provide alternative compounds useful in the therapy of pain, in general, and more particularly, in the treatment of neuropathic pain or allodynia. Likewise, it would be highly desirable to dispose of new compounds which potentiate the analgesic effect of opioids and opiates.

BRIEF DESCRIPTION OF THE INVENTION

The inventors of the present invention have surprisingly found a family of pyrazole derivatives which are particularly effective in the therapy of pain. Further, they have demonstrated that the administration of these new compounds in conjunction with an opioid or opiate may surprisingly potentiate synergistically the analgesic effects of the latter.

Therefore, one aspect of the invention relates to compounds having the formula (I):

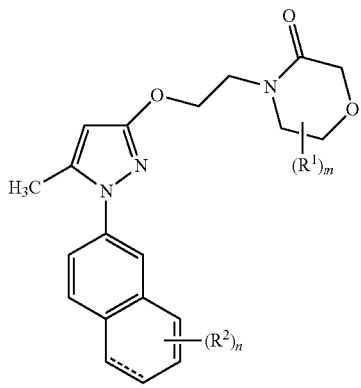

wherein
R$^1$ and R$^2$ are independently selected from the group consisting of substituted or unsubstituted C$_{1-6}$alkyl, halogen, hydroxy and C$_{1-6}$alkoxy;
n and m are independently selected from 0, 1, and 2;
the dashed line (represented by - - - - - ) represents an optional double bond or a pharmaceutically acceptable salt, isomer, prodrug or solvate thereof.

Another aspect of this invention refers to processes for the preparation of a compound of formula (I) as defined above or a pharmaceutically acceptable salt, isomer, prodrug or solvate thereof.

Another aspect of this invention refers to a medicament or pharmaceutical composition comprising at least one compound of formula (I) as defined above, or a pharmaceutically acceptable salt, isomer, prodrug or solvate thereof and a pharmaceutically acceptable carrier, adjuvant or vehicle.

Another aspect of this invention refers to a compound of formula (I) as defined above, or a pharmaceutically acceptable salt, isomer, prodrug or solvate thereof, for use as a medicament, particularly for the prevention and/or treatment of pain.

Another aspect of this invention refers to a combination for simultaneous, separate or sequential administration comprising at least one compound of formula (I) as defined above, or a pharmaceutically acceptable salt, isomer, prodrug or solvate thereof, and at least one opioid or opiate, for use in the prevention and/or treatment of pain.

Another aspect of this invention refers to the use of a compound of formula (I) or a combination as defined above in the manufacture of a medicament for the prevention and/or treatment of pain.

Another aspect of the present invention refers to a method for the treatment and/or prophylaxis of pain, the method comprising administering to the subject in need of such a treatment or prophylaxis a therapeutically effective amount of a compound of formula (I) or a combination as defined above.

Another aspect of the present invention refers to a compound of formula (I) as defined above, or a pharmaceutically acceptable salt, isomer, prodrug or solvate thereof, for use in potentiating the analgesic effects of an opioid or opiate.

Another aspect of the present invention refers to the use of a compound of formula (I) as defined above, or a pharmaceutically acceptable salt, isomer, prodrug or solvate thereof for manufacturing a medicament for potentiating the analgesic effects of an opioid or opiate.

These aspects and preferred embodiments thereof are additionally also defined in the claims.

DETAILED DESCRIPTION OF THE INVENTION

Figure 1:
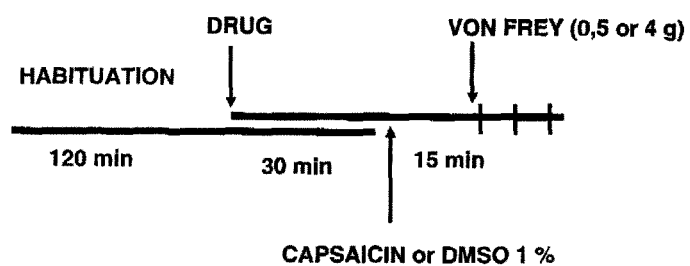
FIG. 1: Test protocol for all tests with von Frey filaments.

In the context of the present invention, the following terms have the meaning detailed below.

As used herein C$_{1-6}$alkyl, as a group or part of a group, defines straight or branched chain saturated hydrocarbon radicals having from 1 to 6 carbon atoms such as methyl, ethyl, n-propyl, i-propyl, n-butyl, t-butyl, pentyl, hexyl, and 2-methylbutyl. Likewise, C$_{1-4}$alkyl, as a group or part of a group, defines straight or branched chain saturated hydrocarbon radicals having from 1 to 4 carbon atoms. Alkyl radicals may be optionally substituted by one or more substituents such as a aryl, halo, hydroxy, alkoxy, carboxy, cyano, carbonyl, acyl, alkoxycarbonyl, amino, nitro, mercapto, alkylthio, etc. If substituted by aryl we have an "Aralkyl" radical, such as benzyl and phenethyl.

The term C$_{1-6}$alkoxy means C$_{1-6}$alkyloxy or a C$_{1-6}$alkyl ether radical, wherein the term C$_{1-6}$alkyl is as defined above. Likewise, the term C$_{1-4}$alkoxy means C$_{1-4}$alkyloxy or a C$_{1-4}$alkyl ether radical, wherein the term C$_{1-4}$alkyl is as defined above. Examples of suitable alkyl ether radicals include methoxy, ethoxy, n-propoxy, iso-propoxy, n-butoxy, iso-butoxy, sec-butoxy, tert-butoxy, and hexanoxy.

"Halogen", "halo" or "hal" refer to bromo, chloro, iodo or fluoro.

It should be noted that the radical positions on any molecular moiety used in the definitions may be anywhere on such moiety as long as it is chemically stable.

Radicals used in the definitions of any variable herein include all possible isomers unless otherwise indicated.

The term "salt" must be understood as any form of an active compound used in accordance with this invention in which said compound is in ionic form or is charged and coupled to a counter-ion (a cation or anion) or is in solution. This definition also includes quaternary ammonium salts and complexes of the active molecule with other molecules and ions, particularly, complexes formed via ionic interactions. The definition includes in particular physiologically acceptable salts; this term must be understood as equivalent to "pharmacologically acceptable salts" or "pharmaceutically acceptable salts".

The term "pharmaceutically acceptable salts" in the context of this invention means any salt that is tolerated physiologically (normally meaning that it is not toxic, particularly, as a result of the counter-ion) when used in an appropriate manner for a treatment, applied or used, particularly, in humans and/or mammals. These physiologically acceptable salts may be formed with cations or bases and, in the context of this invention, are understood to be salts formed by at least one compound used in accordance with the invention—normally an acid (deprotonated)—such as an anion, particularly when used on humans and/or mammals. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bonded by a non-covalent bond to another molecule (normally a polar solvent), including especially hydrates and alcoholates, like for example, methanolate. A preferred solvate is the hydrate.

Any compound that is a prodrug of a compound of formula (I) is also within the scope of the invention. The term "prodrug" is used in its broadest sense and encompasses those derivatives that are converted in vivo to the compounds of the invention. Examples of prodrugs include, but are not limited to, derivatives and metabolites of the compounds of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley), "Design and Applications of Prodrugs" (H. Bundgaard ed., 1985, Harwood Academic Publishers) and Krogsgaard-Larsen et al. "Textbook of Drug design and Discovery" Taylor & Francis (April 2002).

The compounds of the present invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

Furthermore, any compound referred to herein may exist as tautomers. Specifically, the term tautomer refers to one of two or more structural isomers of a compound that exist in equilibrium and are readily converted from one isomeric form to another. Common tautomeric pairs are amine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}C$- or $^{14}C$-enriched carbon, or the replacement of at least one nitrogen by $^{15}N$-enriched nitrogen are within the scope of this invention.

The compounds of formula (I), or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

As noted previously, the term "pharmaceutically acceptable salts, solvates, prodrugs" refers to any salt, solvate, or any other compound which, upon administration to the recipient is capable of providing (directly or indirectly) a compound as described herein. However, it will be appreciated that non-pharmaceutically acceptable salts, solvates and prodrugs also fall within the scope of the invention since those may be useful in the preparation of pharmaceutically acceptable salts, solvates and prodrugs. The preparation of salts, solvates and prodrugs can be carried out by methods known in the art.

As used herein, the terms "treat", "treating" and "treatment" include the eradication, removal, reversion, alleviation, modification, or control of a disease or condition, such as pain.

As used herein, the terms "prevention", "preventing", "preventive", "prevent" and "prophylaxis" refer to the capacity of a compound of formula (I) to avoid, minimize or difficult the onset or development of a disease or condition, such as pain, before its onset.

Therefore, by "treating" or "treatment" and/or "preventing" or "prevention", as a whole, is meant at least a suppression or an amelioration of the symptoms associated with the condition afflicting the subject, where suppression and amelioration are used in a broad sense to refer to at least a reduction in the magnitude of a parameter, e.g., symptom associated with the condition being treated, such as pain. As such, the method of the present invention also includes situations where the condition is completely inhibited, e.g., prevented from happening, or stopped, e.g., terminated, such that the subject no longer experiences the condition. As such, the present method includes both preventing and managing pain, particularly, neuropathic pain, such as hyperalgesia or allodynia.

As used herein, the term "potentiating the analgesic effect of an opioid or opiate" refer to the increase in the affectivity of the analgesic effect of said opioids or opiates produced by compounds of formula (I). In an embodiment of the invention said potentiating effect induces an increase in the analgesic effect of opioids by a factor of 1.2, 1.5, 2, 3, 4 or more, even in some case by a factor of 14 or 15, when compared, with the opioids or opiates, or with the compound of formula (I) when administered in isolation. The measurement can be done following any known method in the art. In an embodiment of the invention, the compound of formula (I) potentiates the analgesic effect of an opioid or opiate by a factor of at least 1.2 when measured in a mechanical allodynia rat model or in a in a thermal hyperalgesia rat model. In a further embodiment, said factor is of at least 1.5, 2, 3, 4 or more, even in some case by a factor of 14 or 15.

In the compounds of formula (I) or subgroups thereof, the substituent $R^1$ and $R^2$ may be bonded to any carbon atom of the corresponding ring. Therefore, in the compounds of formula (I) or subgroups thereof, the substituent $R^1$ may be bonded to any carbon of the morpholinone ring, for example, the substituent R¹ may be bonded to any one of carbons 2, 5 or 6, as depicted hereinafter:

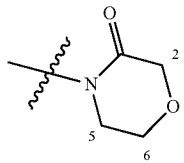

Likewise, in the compounds of formula (I) or subgroups thereof, the substituent R² may be bonded to any carbon atom of the naphthyl or the 5,6-dihydronaphthalenyl ring, for example, the substituent R² may be bonded to any one of carbon atoms 1, 3, 4, 5, 6, 7, or 8, as depicted hereafter:

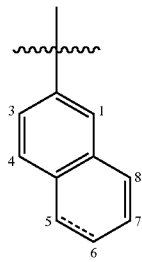

In a particular variant of the invention, the dashed line (represented by represents a double bond in the formula (I) or subgroups thereof.

In a particular embodiment, n and m are 0, i.e., the compound of formula (I) is 4-(2-(5-methyl-1-(naphthalen-2-yl)-1H-pyrazol-3-yloxy)ethyl) morpholin-3-one.

In another embodiment, R¹ is hydroxy.

In another embodiment, R² is substituted or unsubstituted alkyl, preferably $C_{1-4}$alkyl, and more preferably methyl. If substituted, alkyl is preferably substituted with hydroxy. Accordingly, hydroxymethyl is a preferred radical.

In another embodiment, R² is $C_{1-6}$alkoxy, preferably $C_{1-4}$alkoxy, and more preferably methoxy.

According to a particular embodiment, halogen is preferably, bromo or fluoro more preferably as R² in the compounds of the invention.

In additional preferred embodiments, the preferences described above for the different substituent are combined. The present invention is also directed to such combinations of preferred substitutions in the formulae above.

Particular individual compounds of the invention falling under formula (I) include the compounds listed below:

4-(2-(5-methyl-1-(naphthalen-2-yl)-1H-pyrazol-3-yloxy)ethyl)morpholin-3-one
4-(2-(1-(8-hydroxynaphthalen-2-yl)-5-methyl-1H-pyrazol-3-yloxy)ethyl)morpholin-3-one
4-(2-(1-(6-hydroxynaphthalen-2-yl)-5-methyl-1H-pyrazol-3-yloxy)ethyl)morpholin-3-one
4-(2-(1-(7-methoxynaphthalen-2-yl)-5-methyl-1H-pyrazol-3-yloxy)ethyl)morpholin-3-one
4-(2-(1-(7-hydroxynaphthalen-2-yl)-5-methyl-1H-pyrazol-3-yloxy)ethyl)morpholin-3-one
6-hydroxy-4-(2-(5-methyl-1-(naphthalen-2-yl)-1H-pyrazol-3-yloxy)ethyl)morpholin-3-one
4-(2-(1-(5,6-dimethoxynaphthalen-2-yl)-5-methyl-1H-pyrazol-3-yloxy)ethyl)morpholin-3-one
4-(2-(1-(6-methoxynaphthalen-2-yl)-5-methyl-1H-pyrazol-3-yloxy)ethyl)morpholin-3-one
4-(2-(1-(6-fluoronaphthalen-2-yl)-5-methyl-1H-pyrazol-3-yloxy)ethyl)morpholin-3-one
4-(2-(1-(6-bromonaphthalen-2-yl)-5-methyl-1H-pyrazol-3-yloxy)ethyl)morpholin-3-one
4-(2-(5-methyl-1-(6-methylnaphthalen-2-yl)-1H-pyrazol-3-yloxy)ethyl)morpholin-3-one
4-(2-(1-(6-(hydroxymethyl)naphthalen-2-yl)-5-methyl-1H-pyrazol-3-yloxy)ethyl)morpholin-3-one
4-(2-(1-(4-fluoronaphthalen-2-yl)-5-methyl-1H-pyrazol-3-yloxy)ethyl)morpholin-3-one
4-(2-(1-(5,6-dihydroxy-5,6-dihydronaphthalen-2-yl)-5-methyl-1H-pyrazol-3-yloxy)ethyl)morpholin-3-one
or a pharmaceutically acceptable salt, isomer, prodrug or solvate thereof.

The compounds of formula (I) defined above can be obtained by available synthetic procedures. For example, they can be prepared by reacting a compound of formula (II):

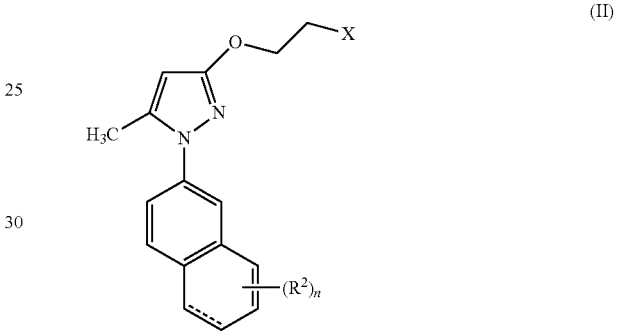

in which R² and n are as defined above in formula (I), and X is a leaving group, preferably chlorine or pyridinium, with a compound of formula (III):

in which R¹ and m are as defined above in formula (I).

The reaction of compounds of formulas (II) and (III) is preferably carried out in an aprotic solvent, but not limited to, such as dimethylformamide (DMF) in the presence of an inorganic base, such as $K_2CO_3$. Compounds of formula (III) are commercially available or can be prepared by conventional methods.

The obtained compounds, when necessary, can be collected from the reaction mixture according to the methods known in the art. For example, when insoluble materials are present, the desired compound can be obtained—after removing the insoluble materials by filtration—by removing the solvent, e.g. by removing the solvent under reduced pressure, and/or by adding water to the residue and extracting the mixture with a water-immiscible organic solvent such as ethyl acetate, etc. Optionally, the desired compound can be obtained after drying over anhydrous sodium sulfate, for instance, and further, if necessary, by purifying with any conventional method, such as recrystallization, column chromatography, or other techniques.

It is evident that in the foregoing and in the exemplified reactions, the reaction products may be isolated from the reaction medium and, if necessary, further purified by methods generally known in the art, such as extraction, crystallization, trituration and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

Many compounds comprised by formula (I) may be converted into each other following functional group transformation reactions well known in the art. Preferably, they are obtained by utilizing suitable starting materials, like for example, compounds of formula (II) and (III) including already the desired substituents.

In particular, in those compounds with hydroxy substitutents as $R^1$ or $R^2$, such hydroxy moieties may be converted into the corresponding $C_{1-6}$ alkoxy by reacting the compounds with an $C_{1-6}$alkyl halide in the presence of a base, such as an alkali of alkaline metal hydride, like lithium hydride or sodium hydride, or an alkali metal alkoxide, like sodium or potassium methoxide or ethoxide, potassium tert-butoxide, or potassium carbonate, triethylamine, pyridine, sodium iodide, cesium carbonate, etc. The $C_{1-6}$alkyl halide may be selected, for instance, from methyl or ethyl iodide.

In addition, in those compounds with $C_{1-6}$alkoxy substitutents as $R^1$ or $R^2$, such $C_{1-6}$alkoxy moieties may be converted into the corresponding hydroxy by submitting the relevant compounds to acidic conditions, such as with hydrochloric acid, hydrobromic acid, or hydroiodic acid.

It has been found that the compounds of general formula (I) are useful in the treatment of pain. In a particular embodiment of the present invention, the pain is neuropathic pain. More preferably, the pain is hyperalgesia or allodynia.

The present invention further provides medicaments or pharmaceutical compositions comprising a compound of this invention, or a pharmaceutically salt, derivative, prodrug or stereoisomer thereof together with a pharmaceutically acceptable carrier, adjuvant, or vehicle, for administration to a patient.

The auxiliary materials or additives of a pharmaceutical composition according to the present invention can be selected among carriers, excipients, support materials, lubricants, fillers, solvents, diluents, colorants, flavour conditioners such as sugars, antioxidants, binders, adhesives, disintegrants, anti-adherents, glidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The medicament or pharmaceutical composition according to the present invention may be in any form suitable for the application to humans and/or animals, preferably humans including infants, children and adults and can be produced by standard procedures known to those skilled in the art. Therefore, the formulation in accordance with the invention may be adapted for topical or systemic application, particularly for dermal, transdermal, subcutaneous, intramuscular, intra-articular, intraperitoneal, intravenous, intra-arterial, intravesical, intraosseous, intracavernosal, pulmonary, buccal, sublingual, ocular, intravitreal, intranasal, percutaneous, rectal, vaginal, oral, epidural, intrathecal, intraventricular, intracerebral, intracerebroventricular, intracisternal, intraspinal, perispinal, intracranial, delivery via needles or catheters with or without pump devices, or other application routes.

In a preferred embodiment the pharmaceutical compositions are in oral form, either solid or liquid. Suitable dose forms for oral administration may be tablets, pills, caplets, gel caps, chewing gums, capsules, granules, drops, syrups or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or reconstitutable dry preparations, aerosols or sprays in the appropriate unit dosage form. Adequate excipients can be used, such as bulking agents, buffering agents or surfactants.

The composition of the invention may be formulated as deposits in dissolved form or in patches, for percutaneous application.

Skin applications include ointments, gels, creams, lotions, suspensions or emulsions.

Suitable form of rectal application is by means of suppositories.

The mentioned formulations will be prepared using standard methods such as those described or referred to in the Spanish and US Pharmacopoeias and similar reference texts.

In one embodiment of the invention it is preferred that compound of formula (I) is used in therapeutically effective amounts. The physician will determine the dosage of the present therapeutic agents which will be most suitable and it will vary with the form of administration and the particular compound chosen, and furthermore, it will vary with the patient under treatment, the age of the patient, the type of disease or condition being treated. When the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents. Active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Particularly, the combination of at least one compound of formula (I) and at least one opioid or opiate may be formulated for its simultaneous, separate or sequential administration, with at least a pharmaceutically acceptable carrier, additive, adjuvant or vehicle. This has the implication that the combination of the compound of formula (I) and the opioid or opiate may be administered:

a) As a combination that is being part of the same medicament formulation, both being then administered always simultaneously.

b) As a combination of two units, each with one of them giving rise to the possibility of simultaneous, sequential or separate administration. In a particular embodiment, the compound of formula (I) is independently administered from the opioid or opiate (i.e in two units) but at the same time. In another particular embodiment, the compound of formula (I) is administered first, and then the opioid or opiate is separately or sequentially administered. In yet another particular embodiment, the opioid or opiate is administered first, and then the compound of formula (I) is administered, separately or sequentially, as defined.

As noted above, a compound of formula (I), or a pharmaceutically acceptable salt, isomer, prodrug or solvate thereof, is useful for potentiating the analgesic effects of an opioid or opiate.

According to the present invention the dosage of the opioid or opiate can be reduced when combined with a compound of formula (I), and therefore attaining the same analgesic effect with a reduced dosage. The compounds of formula (I) may induce an increase in the analgesic effect of opioids of a factor of 1.2, 1.5, 2, 3, 4 or more, even in some case by a factor of 14 or 15.

A preferred embodiment of the present invention comprises the use of a combination of 4-(2-(5-methyl-1-(naphthalen-2-yl)-1H-pyrazol-3-yloxy)ethyl)morpholin-3-one and morphine or tramadol. In a preferred embodiment of the present invention, the opiate utilized is morphine or its analogs. In another preferred embodiment of the present invention, the opioid utilized is tramadol or its analogs.

The following examples are merely illustrative of certain embodiments of the invention and cannot be considered as restricting it in any way.

EXAMPLES

Example N° 1

Synthesis of 4-(2-(5-methyl-1-(naphthalen-2-yl)-1H-pyrazol-3-yloxy)ethyl)morpholin-3-one

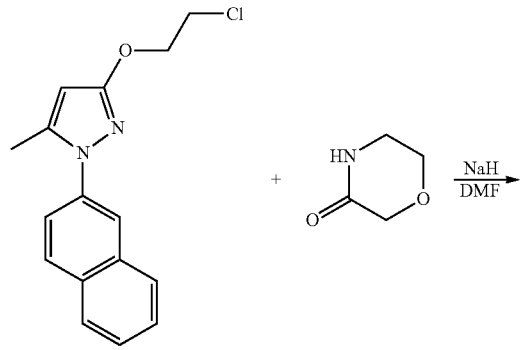

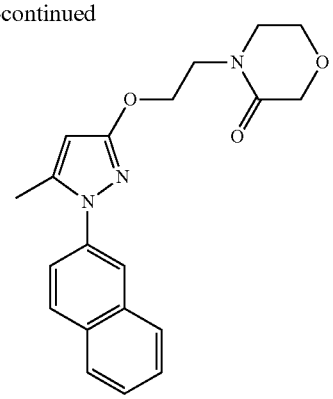

To a stirred suspension of sodium hydride (65 mg 60% dispersion in mineral oil, 1.63 mmol) in DMF (3 ml), cooled to 0-5° C., a solution of morpholin-3-one (91 mg, 0.91 mmol) in DMF (3 ml) was added dropwise. The mixture was stirred at room temperature for 3 hrs. Then, a solution of 3-(2-chloroethoxy)-5-methyl-1-(naphthalen-2-yl)-1H-pyrazole (200 mg, 0.7 mmol) in DMF (4 ml) was added and the mixture was heated to 50° C. for 14 hrs. The reaction mixture was cooled, water (2 ml) added dropwise, and it was evaporated to dryness in vacuum. The resulting residue was partitioned between dichloromethane and water. The organic layer was washed with water, dried over $Na_2SO_4$, filtered and evaporated giving 223 mg of crude residue, which was purified by a silica gel column chromatography (eluent: ethyl acetate) and 4-(2-(5-methyl-1-(naphthalen-2-yl)-1H-pyrazol-3-yloxy)ethyl)morpholin-3-one (192 mg, 78%) was obtained as an amorphous white solid.

Purity determined by HPLC: 100%

$^1$H-NMR (CDCl$_3$) δ ppm: 7.95-7.8 (m, 4H), 7.6-7.5 (m, 3H), 5.7 (s, 1H), 4.45 (t, J=5.2 Hz, 2H), 4.2 (s, 2H), 3.85 (t, J=5.3 Hz, 2H), 3.8 (t, J=5.3 Hz, 2H), 3.6 (t, J=5.4 Hz, 2H), 2.35 (s, 3H).

Pharmacological Data

Effect on Capsaicin in Development of Mechanical Allodynia

This model uses the von-Frey Filaments and is a model to test the effects or symptoms of neuropathic pain, allodynia etc.

Interest of the model:

The injection of 1 µg of capsaicin to experimental animals produces acute pain followed by hyperalgesia/allodynia The mechanisms involved in capsaicin-induced acute pain and hyperalgesia are relatively well known (mainly activation of peripheral nociceptors and sensitization of spinal cord neurons, respectively)

FIG. 1 shows the test protocol for all tests with von Frey filaments. After habituation mice were according to FIG. 1 first treated with the test-compound (or solvent in controls). Then 1 µg capsaicin (1% DMSO) is injected into their paw resulting in developing pain in the effected paw. The effected paw is then treated with a mechanical stimulus and the latency time before the paw is withdrawn is measured.

Figure 2:
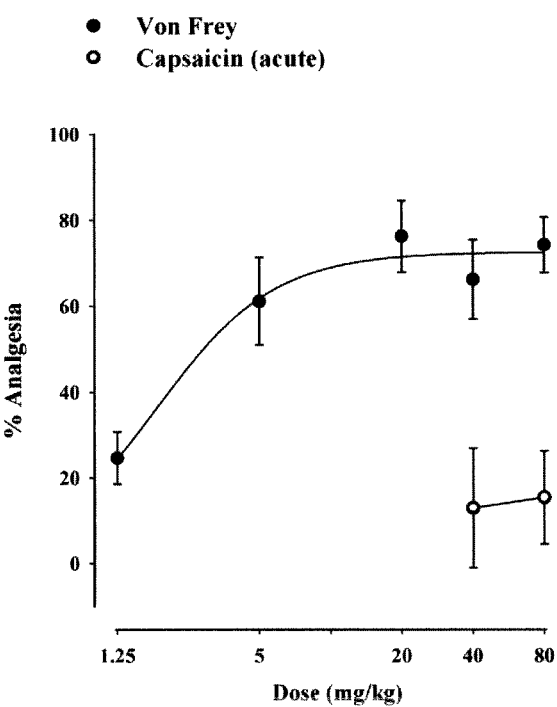
FIG. 2: Chronic analgesia test of Example n° 1 versus Capsaicin (acute test).

This pharmacological test showed the effect of the compound of example 1 in the model described. As shown in FIG. 2 there is a dose dependency of the treatment with the compound of example 1 showing analgesia in capsaicin-induced neuropathic pain.

Effects of Example N° 1 in the Tail-Flick Test in Mice

Modulation of Morphine Analgesia

Materials and Methods

Animals

Male CD1 wild type mice were purchased from Charles-River (France). Animals were housed in groups of ten, provided with food and water ad libitum and kept in controlled laboratory conditions with the temperature maintained at 21±1° C. and light in 12-hour light/dark cycles (on at 07:00 am and off at 07:00 pm). Animals from 6 to 8 weeks old were used. Experiments were carried out between 9:00 am and 15:00 pm in a soundproof, air-regulated experimental room. All experimental procedures and animal husbandry were conducted according to ethical principles for the evaluation of pain in conscious animals (Zimmermann, 1983) and to the European Communities Council Directive of 24 Nov. 1986 (86/609/ECC). The experimental work was approved by the local Ethical Committee.

Drugs

The following drugs were used: Example n° 1 (synthesized by Laboratorios Dr. Esteve S. A., Spain) and morphine hydrochloride (provided by *Agenda Española de medicamentos y productos sanitarios, Area Estupefacientes*). Drugs were dissolved in (hydroxypropyl)methyl cellulose (HPMC, 0.5%) (H9262, Sigma-Aldrich). Morphine was administered in a volume of 5 ml/kg of body weight through the subcutaneous (s.c.) and Example n° 1 was administered in a volume of 10 ml/kg of body weight through the intraperitoneal route (i.p.). The doses of drugs refer to their salt forms.

Nociceptive Assay

Tail-Flick Test

The test was performed as previously described (Moncada et al., 2003). Briefly, the animals were restrained in a Plexiglas tube and placed on the tail-flick apparatus (Panlab, LE 7106, Spain). A noxious beam of light was focussed on the tail about 3 cm from the tip, and the tail-flick latency (TFL, latency or tail removal from the radiant heat source) was recorded automatically to the nearest 0.1 s. The intensity of the radiant heat source was adjusted to yield baseline latencies between 2 and 4 s. A cut-off time was set at 10 s to avoid heat-related damage. The animals received two injections at the same time: HPMC (i.p.)+HPMC (s.c.), HPMC (i.p.)+morphine (2 mg/kg, s.c.), Example n° 1 (5, 10, 20 mg/kg, i.p.)+HPMC (s.c.), or Example n° 1 (5, 10, 20 mg/kg, i.p.)+(2 mg/kg, s.c.), and tail flick latencies were measured 30 min post-administration. All experiments were performed under blind conditions.

Data and Statistical Analysis

Data were expressed as means±S.E.M of the tail flick latency in seconds (s). In order to generate dose-response curves, data were also converted to % Analgesia. By comparison with the mean of vehicle treated group (defined as 0% Analgesia) and the cut-off (prefixed at 10 s) (defined as 100% Analgesia) individual percentages of Analgesia were determined by the formula:

% Analgesia=[(Test Latency−Vehicle Latency)/(Cut-off Latency−Vehicle Latency)]×100

"Example n° 1+morphine" treatment groups were compared with "Example n° 1+vehicle" groups using two-way ANOVA followed by Bonferroni post-hoc test. Statistical analyses were performed with GraphPad Prism version 4 program (GraphPad software, San Diego, Calif.). Statistical significance was set at the 95% confidence level (two tailed) (*$p<0.05$, $p<0.01$, *$p<0.001$). N=8-12 animals/group.

Results

Figure 3:
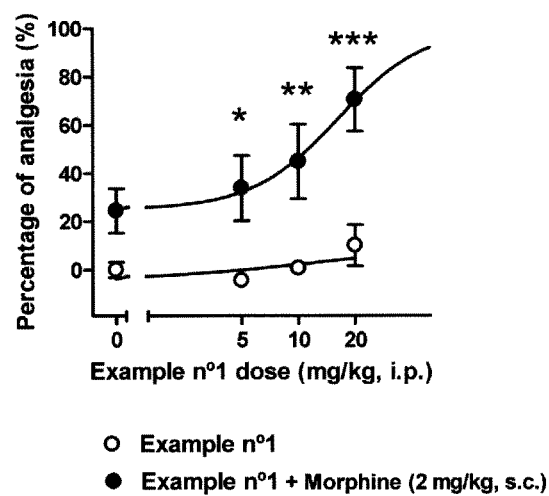
FIG. 3: Potentiation of morphine analgesia by Example n° 1 in the tail-flick test in mice. Coadministration of different doses of Example n° 1 (5-20 mg/kg, i.p.) with a fixed dose of morphine (2 mg/kg, s.c.) dose-dependently increased the analgesic efficacy of morphine. Each symbol is the mean of percentages of analgesia±S.E.M. (N=8-12 mice/group). $p<0.05$, $p<0.01$, $*p<0.001$ "Example n° 1+morphine" vs. "Example no 1+vehicle" groups (Bonferroni Multiple comparison Test post-ANOVA).

As shown in FIG. 3, Example n° 1 enhances the analgesic effect of a fixed dose of morphine in the tail-flick test in mice.

The invention claimed is:

1. A compound of the formula (I)

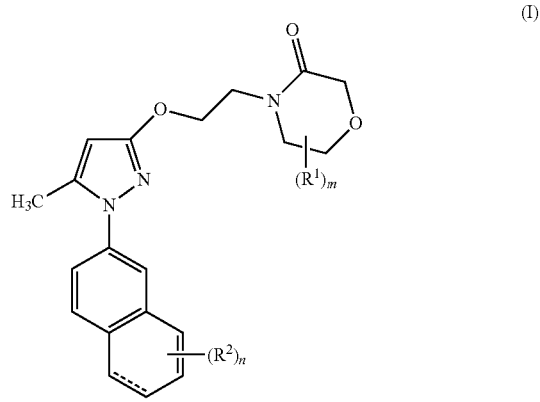

wherein
R$^1$ and R$^2$ are independently selected from the group consisting of substituted or unsubstituted C$_{1-6}$alkyl, halogen, hydroxy and C$_{1-6}$alkoxy;
n and m are independently selected from 0, 1, and 2;
the dashed line (represented by - - - - - ) represents an optional double bond
or a pharmaceutically acceptable salt, isomer, prodrug or solvate thereof.

2. The compound according to claim 1, wherein the dashed line (represented by - - - - - ) represents a double bond.

3. The compound according to claim 1, wherein R$^1$ is hydroxy.

4. The compound according to claim 1, wherein R$^2$ is substituted or unsubstituted C$_{1-4}$alkyl, preferably methyl or hydroxymethyl.

5. The compound according to claim 1, wherein R$^2$ is C$_{1-4}$alkoxy, preferably methoxy.

6. The compound according to claim 1, wherein R$^2$ is bromo or fluoro.

7. The compound according to claim 1, wherein said compound is:
4-(2-(5-methyl-1-(naphthalen-2-yl)-1H-pyrazol-3-yloxy)ethyl)morpholin-3-one;
4-(2-(1-(8-hydroxynaphthalen-2-yl)-5-methyl-1H-pyrazol-3-yloxy)ethyl)morpholin-3-one;
4-(2-(1-(6-hydroxynaphthalen-2-yl)-5-methyl-1H-pyrazol-3-yloxy)ethyl)morpholin-3-one;
4-(2-(1-(7-methoxynaphthalen-2-yl)-5-methyl-1H-pyrazol-3-yloxy)ethyl)morpholin-3-one;

4-(2-(1-(7-hydroxynaphthalen-2-yl)-5-methyl-1H-pyrazol-3-yloxy)ethyl)morpholin-3-one;
6-hydroxy-4-(2-(5-methyl-1-(naphthalen-2-yl)-1H-pyrazol-3-yloxy)ethyl)morpholin-3-one;
4-(2-(1-(5,6-dimethoxynaphthalen-2-yl)-5-methyl-1H-pyrazol-3-yloxy)ethyl)morpholin-3-one;
4-(2-(1-(6-methoxynaphthalen-2-yl)-5-methyl-1H-pyrazol-3-yloxy)ethyl)morpholin-3-one;
4-(2-(1-(6-fluoronaphthalen-2-yl)-5-methyl-1H-pyrazol-3-yloxy)ethyl)morpholin-3-one;
4-(2-(1-(6-bromonaphthalen-2-yl)-5-methyl-1H-pyrazol-3-yloxy)ethyl)morpholin-3-one;
4-(2-(5-methyl-1-(6-methylnaphthalen-2-yl)-1H-pyrazol-3-yloxy)ethyl)morpholin-3-one;
4-(2-(1-(6-(hydroxymethyl)naphthalen-2-yl)-5-methyl-1H-pyrazol-3-yloxy)ethyl)morpholin-3-one;
4-(2-(1-(4-fluoronaphthalen-2-yl)-5-methyl-1H-pyrazol-3-yloxy)ethyl)morpholin-3-one; or
4-(2-(1-(5,6-dihydroxy-5,6-dihydronaphthalen-2-yl)-5-methyl-1H-pyrazol-3-yloxy)ethyl)morpholin-3-one;
or a pharmaceutically acceptable salt, isomer, prodrug or solvate thereof.

8. A combination for simultaneous, separate or sequential administration comprising at least one compound of formula (I) as defined in claim 1, or a pharmaceutically acceptable salt, isomer, prodrug or solvate thereof, and at least one opioid or opiate.

9. A process for the preparation of a compound of formula (I) as defined in claim 1 or a pharmaceutically acceptable salt, isomer, prodrug or solvate thereof, which comprises reacting a compound of formula (II):

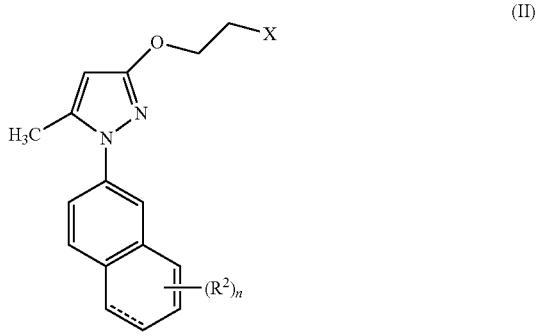

(II)

in which $R^2$ and n are as defined above in formula (I), and X is a leaving group, preferably chlorine or pyridinium, with a compound of formula (III):

(III)

in which $R^1$ and m are as defined above in formula (I).

10. A pharmaceutical composition comprising at least one compound of formula (I) as defined in any of claim 1, or a pharmaceutically acceptable salt, isomer, prodrug or solvate thereof and a pharmaceutically acceptable carrier, adjuvant or vehicle.

11. The compound according to claim 4, wherein $R^2$ is methyl or hydroxymethyl.

12. The compound according to claim 5, wherein $R^2$ is methoxy.

13. The combination according to claim 8, wherein the at least one compound of formula (I) comprises one of the following conditions (a) to (e):
(a) the dashed line (represented by - - - - - ) represents a double bond;
(b) $R^1$ is hydroxyl;
(c) $R^2$ is substituted or unsubstituted
(d) $R^2$ is $C_{1-4}$ alkoxy; and
(e) $R^2$ is bromo or fluoro.

14. The combination according to claim 8, wherein the at least one compound of formula (I) is:
4-(2-(5-methyl-1-(naphthalen-2-yl)-1H-pyrazol-3-yloxy)ethyl)morpholin-3-one;
4-(2-(1-(8-hydroxynaphthalen-2-yl)-5-methyl-1H-pyrazol-3-yloxy)ethyl)morpholin-3-one;
4-(2-(1-(6-hydroxynaphthalen-2-yl)-5-methyl-1H-pyrazol-3-yloxy)ethyl)morpholin-3-one;
4-(2-(1-(7-methoxynaphthalen-2-yl)-5-methyl-1H-pyrazol-3-yloxy)ethyl)morpholin-3-one;
4-(2-(1-(7-hydroxynaphthalen-2-yl)-5-methyl-1H-pyrazol-3-yloxy)ethyl)morpholin-3-one;
6-hydroxy-4-(2-(5-methyl-1-(naphthalen-2-yl)-1H-pyrazol-3-yloxy)ethyl)morpholin-3-one;
4-(2-(1-(5,6-dimethoxynaphthalen-2-yl)-5-methyl-1H-pyrazol-3-yloxy)ethyl)morpholin-3-one;
4-(2-(1-(6-methoxynaphthalen-2-yl)-5-methyl-1H-pyrazol-3-yloxy)ethyl)morpholin-3-one;
4-(2-(1-(6-fluoronaphthalen-2-yl)-5-methyl-1H-pyrazol-3-yloxy)ethyl)morpholin-3-one;
4-(2-(1-(6-bromonaphthalen-2-yl)-5-methyl-1H-pyrazol-3-yloxy)ethyl)morpholin-3-one;
4-(2-(5-methyl-1-(6-methylnaphthalen-2-yl)-1H-pyrazol-3-yloxy)ethyl)morpholin-3-one;
4-(2-(1-(6-(hydroxymethyl)naphthalen-2-yl)-5-methyl-1H-pyrazol-3-yloxy)ethyl)morpholin-3-one;
4-(2-(1-(4-fluoronaphthalen-2-yl)-5-methyl-1H-pyrazol-3-yloxy)ethyl)morpholin-3-one; or
4-(2-(1-(5,6-dihydroxy-5,6-dihydronaphthalen-2-yl)-5-methyl-1H-pyrazol-3-yloxy)ethyl)morpholin-3-one;
or a pharmaceutically acceptable salt, isomer, prodrug or solvate thereof.

15. The process according to claim 9, wherein the leaving group is chlorine or pyridinium.

16. A method for the treatment of pain, the method comprising administering to a subject in need of such a treatment a therapeutically effective amount of a compound of formula (I) as defined in claim 1.

17. The method according to claim 16, wherein the pain is selected from the group consisting of neuropathic pain, inflammatory pain and other pain conditions involving allodynia and/or hyperalgesia.

18. The method according to claim 16, wherein the compound of formula (I) potentiates the analgesic effects of an opioid or opiate.

19. The method according to claim 18, wherein the opioid is morphine.

* * * * *